US00PP09802P

United States Patent [19]

Stemkens

[11] Patent Number: Plant 9,802

[45] Date of Patent: Feb. 11, 1997

[54] GERANIUM PLANT NAMED 'SANLILAC'

[75] Inventor: Henricus G. W. Stemkens, Hoorn, Netherlands

[73] Assignee: S&G Seeds B.V., Enkhuizen, Netherlands

[21] Appl. No.: 572,561

[22] Filed: Dec. 14, 1995

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 3,888 5/1976 Duffett et al. ..... Plt./87.12

*Primary Examiner*—Howard J. Locker

*Attorney, Agent, or Firm*—Lynn Marcus-Wyner

[57] ABSTRACT

A new ivy-leaved geranium particularly distinguished by its well-branched shape and compact growth, early appearing lilac single flowers which do not set seed with good precocity and floral richness.

1 Drawing Sheet

BACKGROUND OF THE NEW PLANT

The present invention comprises a new distinct cultivar of ivy-leaved geranium, botanically known as *Pelargonium peltatum* hybrid. The new cultivar is propagated from cuttings resulting from the cross of I356 and M167. I356 is a lilac flowering peltatum having no pollen. I356 is not commercially available and is not known by any synonyms. M167 is also a lilac colored peltatum, with vigorous growth and having pollen. M167 is not commercially available and is not known by any synonyms. Neither I356 or M167 have been patented. As a result of this cross the present cultivar was created in 1991 in Enkhuizen, Netherlands and has been repeatedly asexually reproduced by cuttings in Enkhuizen, Netherlands and Stuttgart, Germany over a three year period. It has been found to retain its distinctive characteristics through successive propagations, and this novelty appears to be firmly fixed.

DESCRIPTION OF THE DRAWING

This new geranium plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new geranium. The data which defines these characteristics were collected from asexual reproductions carried out in Enkhuizen, Netherlands. The plant history was taken on 12 week old plants, blossomed under natural light in a greenhouse. Color readings were taken in the greenhouse under ambient light. Color references are primarily to the RHS Color Chart of the Royal Horticultural Society of London.

The Plant

Classification:

*Botanical.*—*Pelargonium peltatum*—Hybrid.

*Commericial.*—Ivy-leaved geranium.

Parentage:

*Female parent.*—A seedling named I356 is one of our seedlings from our I-generation of plants bred in 1984.

*Pollen parent.*—A seedling named M167 is one of our seedlings from M-generation of plants bred in 1988.

Form: Very compact, hanging.

Shape: Round.

Stalk length: About 160–210 mm in April and 420–510 mm in September.

Number of stems per stalk: Approximately 6–8 from May until the end of September.

Number of stalks per plant: Approximately 9–11 in October.

Internode length: About 42–78 mm depending on the light where the plant is propagated.

Growth rate: Hanging and vigorous.

Strength: Very good.

Branching character: Very good branching.

Foliage:

*Quantity.*—Many robust leaves.

*Size.*—Small, from 48–64 mm.

*Shape.*—5 lobed, peltate.

*Texture.*—Hairy at young leaf stage (1 cm long), becoming smoother with increased maturity.

*Zonation.*—Almost circular, diameter 2 mm, brown.

Ribs and veins: 7 Ribs.

Color:

*Upper side.*—Medium green 141A.

*Lower side.*—Light green 137C.

Length of leaf stem: 25–55 mm.

The Bud

Peduncle length: 90–125 mm, depending on the season.

Size:

*Diameter.*—3 mm.

*Length.*—11 mm.

Shape: Elliptical.

Form: Ovoid and pointed.

Rate of opening: Medium.

Color:

*When sepals first divide.*—137C.

*When petals begin to unfurl.*—138A.

Sepals:

*Color.*—Inside — 138B. Outside — 138A.

*Form.*—Standing up.

Pedicel:

*Length.*—About 20–26 mm.

*Strength.*—Very strong, the florets are arranged asymmetric around the middle of the cluster. The florets are approximately 38 mm in diameter.

*Color.*—Red purple 183A.

Blooming habit: Continuous and profusely from April until October.

Size: Approximately 70–80 mm.
Borne: In a cluster having between 4–6 flowers per cluster.
Form: Horizontal symmetric, quite open. When the flowers mature, the petals curl back.
Petals:
*Numbers.*—5 per floret, between 110–130 clusters in one season per plant.
*Arrangement.*—2 upper petals, longer and broader. 3 lower petals, smaller.
*Form.*—Upper obcordate.
*Color.*—Outer petal —77D, very light red purple. Inside petal — 76C.
*Markings.*—See pattern.
*Reverse side.*—Pink 69A with red purple nerves colour 59C.
*Pattem.* 'The upper two petals have two long red purple margins (colour 59C) which fade into the veins. Between the end of the two lines there is a small red purple blotch. The reverse side has the same stripes, but lighter in colour. The lower petals have darker colored veins. The outer parts of the petals are pink colored (59D).
Texture: Smooth.
Appearance: Satiny.
Petals remain on stem about 5–7 days depending on the weather.
Persistence: Petals drop, so no picking of matured clusters.
Disease resistance: Sanlilac does not suffer from Botrytis.
Weather resistance: Sanililac is not unusually affected by wet or hot weather.
Lasting quality:
*On the living plant in pot.*—About 10–14 days.
*As a cut flower.*—About 5 days.
Frgrance: No perceptible fragrance.

Reproductive Organs

Stamens:
*Anthers.*—Totally shriveled, and yellow in color.
*Filaments.*—Usually 7, about 1 mm in length, and white in color.
Pollen: None.
Pistils:
*Number.*—One.
*Length.*—Approximately 5 mm.
*Sigmas.*—Pink in color, divided in 5 papillae.
Ovaries: Green in color.
Seed: Non fertile.

What is claimed is:

1. A new and distinct cultivar of ivy-leaved geranium plant substantially as herein shown and described, particularly distinguished by its very short internodes and well branched plant, and its early appearing lilac single flowers which do not set seed.

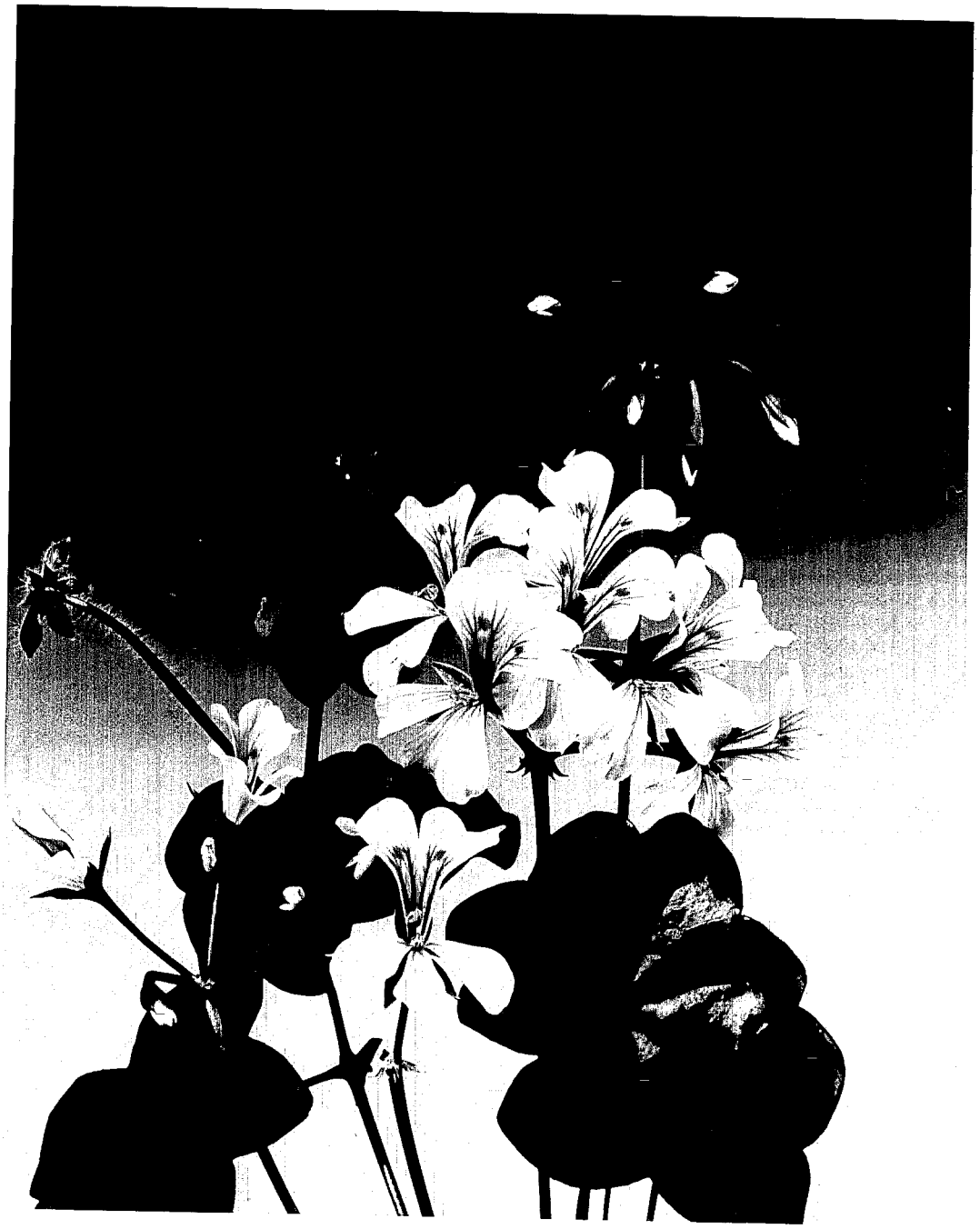

* * * * *